US006207396B1

(12) United States Patent
Sigler et al.

(10) Patent No.: US 6,207,396 B1
(45) Date of Patent: *Mar. 27, 2001

(54) IMMUNOASSAY REAGENTS AND METHODS FOR DETERMINATION OF LSD AND LSD METABOLITES

(75) Inventors: Gerald F. Sigler, Carmel, IN (US); Riaz Rouhani, Concord, CA (US); David Davoudzadeh, Pleasanton, CA (US); William A. Coty, Livermore, CA (US); Jeffrey E. Shindelman, Concord, CA (US); Paul R. Morrill, Cambridge (GB)

(73) Assignee: Microgenics Corporation, Fremont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/026,780

(22) Filed: Feb. 20, 1998

Related U.S. Application Data

(63) Continuation-in-part of application No. 08/560,871, filed on Nov. 20, 1995, now Pat. No. 5,843,682.
(60) Provisional application No. 60/039,018, filed on Feb. 21, 1997, and provisional application No. 60/047,256, filed on May 21, 1997.

(51) Int. Cl.[7] .................. G01N 33/53; G01N 33/532; C07K 16/00; C07D 221/18

(52) U.S. Cl. ................ 435/7.6; 435/7.9; 436/544; 530/387.1; 530/403; 546/61; 546/70; 546/77

(58) Field of Search .............. 435/7.6, 7.9; 436/544, 436/545, 546; 530/387.1, 403; 546/61, 69, 70, 77

(56) References Cited

U.S. PATENT DOCUMENTS

| | | |
|---|---|---|
| 3,218,324 | 11/1965 | Hofmann et al. . |
| 3,249,617 | 5/1966 | Hofmann et al. . |
| 3,249,619 | 5/1966 | Johnston . |
| 4,208,479 | 6/1980 | Zuk et al. . |
| 4,233,401 | 11/1980 | Yoshida et al. . |
| 4,236,893 | 12/1980 | Rice . |
| 4,375,414 | 3/1983 | Strahilevitz . |
| 4,708,929 | 11/1987 | Henderson . |
| 5,037,645 | 8/1991 | Strahilevitz . |
| 5,843,682 | * 12/1998 | Sigler et al. .................. 435/7.6 |

FOREIGN PATENT DOCUMENTS

| | | |
|---|---|---|
| 396024 | 7/1965 | (CH) . |
| 0411495 | 2/1991 | (EP) . |
| 0 816 364 A1 | 1/1998 | (EP) . |
| WO 90/15798 | 12/1990 | (WO) . |
| WO 94/17104 | 8/1994 | (WO) . |
| WO 96/10179 | 4/1996 | (WO) . |
| WO 97/19100 | 5/1997 | (WO) . |

OTHER PUBLICATIONS

Arap, W. et al., "Cancer Treatment by Targeted Drug Delivery to Tumor Vasculature in a Mouse Model" *Science* 279:377–380 (Jan. 16, 1998).

Siddik, Z.H. et al., "The Metabolism of Lysergic Acid Di[$^{14}$C]Ethylamide ([$^{14}$C]LSD) in the Isolated Perfused Rat Liver" *Biochem. Pharmacol.* 28:3081–3091 (1979).

Tijssen, P., "Quantitative Enzyme Immunoassay Techniques" *in*: Practice & Theory of Enzyme Immunoassays, Chapter 14, Elsevier, Amsterdam, pp. 329–384 (1985).

Cody et al., "Immunoassay analysis of lysergic acid diethylamide" *J. Anal. Toxicol.* (1997) 21(6): 459–464.

Altunkaya et al., "Evaluation of a commercial radioimmunoassay kit for the detection of lysergide (LSD) in serum, whole blood, urine and stomach contents" *Forensic Science International* (1990) 47:113–121.

Bellet et al., "Cedia® LSD assay for urine drug testing" *Clin. Chem.* (1996) 42:S226 (abstract No. 545).

Cassells et al., "Development and validation of a nonisotopic immunoassay for the detection of LSD in human urine" *J. Anal. Toxicol.* (1996) 20:409–415.

Castro et al., "LSD Radioimmunoassay" *Res. Commun. Chem. Pathol. Pharmacol.* (1973) 6:879–886.

Hu et al., "Emit® II LSD assay on the SYVA–30R analyzer" *Clin. Chem.* (1996) 42:S219–S220. (abstract No. 517).

Lauderer et al., "Antibodies to lysergic acid diethylamide (LSD–25)" Bull. New Jersey Acad. Sci. (1974) 19(1): 8–10.

Lim et al., "Quantification of LSD and N–Demethyl–LSD in urine by gas chromatography/resonance electron capture ionization mass spectrometry" *Anal. Chem.* (1988) 60:1420–1425.

Lin et al., "Syva Emit® LSD assay" *Clin. Chem.* (1995) 41:S133 (abstract No. 444).

Loeffler et al., "Radioimmunoassay for Lysergide (LSD) in illicit drugs and biological fluids" *J. Pharm. Sci.* (1973) 62:1817–1820.

McCarron et al., "Confirmation of LSD intoxication by analysis of serum and urine" *J. Anal. Toxicol.* (1990) 14:165–167.

(List continued on next page.)

*Primary Examiner*—Jyothsna Venkat
*Assistant Examiner*—P Ponnaluri
(74) *Attorney, Agent, or Firm*—Wood, Herron & Evans, L.L.P.

(57) ABSTRACT

To improve the detection of LSD in biological samples, antibodies are raised to LSD conjugated to a protein carrier, preferably through the indole ring. Selected antibodies are matched with an immunoassay reagent in which the LSD is conjugated in the same position to a labeling or separation means. The set of reagents can be used in immunoassays with remarkably little cross-reactivity with potential interfering substances such as chlorpromazine and ergotamine, and a low false-positive rate in a panel of clinical test samples. Also provided is a set of reagents for measuring glucuronide metabolites of LSD by immunoassay, which permits exposure to LSD to be determined over a longer diagnostic window.

15 Claims, 7 Drawing Sheets

OTHER PUBLICATIONS

News item from *Diagnostics Intelligence* entitled "Behring Introduces LSD-screening assay in U.K.".

Ratcliffe et al., "Radioimmunoassay of lysergic acid diethylamide (LSD) in serum and urine by using antisera of different specificities" *Clin. Chem.* (1977) 23:169–174.

Siddik et al., "The fate of lysergic acid di[14C]ethylamide ([$^{14}$C]LSD) in the rat, guinea pig and rhesus monkey and of [$^{14}$C]iso-LSD in rat" *Biochem. Pharmacol.* (1979) 28:3093–3101.

Smith et al., "Body fluid levels of lysergide (LSD)" *Forensic Science International* (1985) 28:229–237.

Stead et al., "The development and evaluation of a $^{125}$I radioimmunoassay for the measurement of LSD in body fluids" *Forensic Science International* (1986) 32:49–60.

Taunton-Rigby et al., "Lysergic acid diethylamide: Radioimmunoassay" *Science* (1973) 181:165–166.

Twitchett et al., "Analysis of LSD in human body fluids by high-performance liquid chromatography, fluorescence spectroscopy and radioimmunoassay" *J. Chromatography* (1978) 150:73–84.

Vanakis et al., "Specificity of the antibody receptor site to D-lysergamide: Model of a physiological receptor for lysergic acid diethylamide" *Proc. Natl. Acad. Sci. USA* (1971) 68:1483–1487.

Voss et al., "Neutralization of LSD by active immunization" *Psychopharmacologia* (1972) 26:140–145.

Webb et al., "The analysis of lysergide (LDS):The development of novel enzyme immunoassay and immunoaffinity extraction procedures together with an HPLC–MS confirmation procedure" *J. Forensic Sciences* (1996) 41:938–946.

* cited by examiner

IMMUNOASSAY REAGENTS AND METHODS FOR DETERMINATION OF LSD AND LSD METABOLITES

RELATED APPLICATIONS

This application is a continuation-in-part of U.S. application Ser. No. 08/560,871, filed Nov. 20, 1995, now U.S. Pat. No. 5,843,682. This application also claims the priority benefit of provisional applications U.S. application Ser. No. 60/039,018, filed Feb. 21, 1997, now abandoned; and U.S. application Ser. No. 60/047,256, filed May 21, 1997, now abandoned. The aforementioned patent applications are hereby incorporated herein by reference in their entirety.

BACKGROUND OF THE INVENTION

The present invention relates to novel carboxyalkyl 1-position derivatives of lysergic acid diethylamide (LSD) and methods for preparation of these derivatives. The derivatives include immunogens used to stimulate antibody production and polypeptide conjugates useful in immunoassays for detecting LSD. Also provided are hapten intermediates used in the synthesis of the immunogens and polypeptide conjugates and a non-isotopic immunoassay for the determination of LSD.

Although there is widespread public perception that use of LSD is no longer a societal problem, there is considerable evidence that this illicit drug continues to be used, and in some segments of the population, its use is increasing. See Bonner, *Drug Detection Report.* 1:5 (1992). LSD was one of the 20 controlled substances most commonly encountered in emergency rooms across the nation in 1985, reflecting continuing abuse and trafficking of this illicit drug. In the United States, seizures of LSD by the Drug Enforcement Agency doubled in 1990 over the previous year, and in England, seizures of LSD have steadily increased since mid-1988. See *Microgram* 23:228 (1990). Further cause for concern are reports that LSD is particularly popular among adolescents, and in some areas, it exceeds cocaine in popularity. See Seligmann, *Newsweek,* February 3rd, p. 66, (1992). Factors that have contributed to the continued use of LSD are its wide availability, low cost, and the difficulty of detecting LSD use by analysis of body fluids.

Despite the long history of abuse associated with LSD, little is known concerning the disposition of LSD in humans. The lack of pharmacokinetic data on LSD is partly due to the technical difficulty of detecting and measuring the drug in physiological specimens. LSD is not considered highly toxic, although at least two cases where death was apparently a result of LSD toxicity have been reported. However, the major reason many consider LSD to be highly dangerous is that it can have serious psychological and psychotic effects which sometimes cause users to commit irrational acts resulting in injury or death. LSD is an extremely potent psychedelic drug that acts primarily on the central nervous system; only the d-isomer of the drug is pharmacologically active. Oral doses as low as 25 $\mu$g can cause central nervous system disturbances such as hallucinations, distortions in sensory perception, mood changes and dream-like thought processes, as well as psychotic reactions in apparently predisposed individuals. Therefore, concentrations of LSD and LSD metabolites in blood and urine are likely to be very low. The detection of LSD in body fluids of users is especially difficult because the quantities typically ingested are very small and because the drug is rapidly and extensively converted to metabolic products. Furthermore, the drug's low volatility, its thermal instability, and its tendency to undergo adsorptive losses during gas chromatographic analysis all contribute to the difficulty of developing a method for confirmation of LSD in body fluids.

LSD is a natural product of the rye fungus Claviceps and was first prepared synthetically in 1938. Its psychological effects were discovered following accidental ingestion. Chemically, LSD is an ergot alkaloid and, like other compounds of this class, contains lysergic acid as the basis of its structure. Structurally similar to serotonin (5-hydroxytryptamine), LSD is thought to exert its psychotomimetic effects through antagonism of serotonin activity in the brain stem. Little is known about the tissue distribution, metabolism and excretion of LSD in humans. LSD is absorbed fairly rapidly by the gastrointestinal tract, and its plasma half-life has been calculated to be about 3 hours in man. Animal studies indicate that LSD is inactivated via hepatic oxidation. It is extensively metabolized with only negligible amounts of unchanged drug appearing in the urine and feces, with most of the metabolites being excreted in the urine. Possible metabolic transformations may be hydrolysis to lysergic acid, N-demethylation to nor-LSD and oxidation to 2-oxo-LSD. Studies with urine samples from human volunteers receiving LSD demonstrate that the drug or its closely related metabolites can be detected in the urine by radioimmunoassay (RIA) for several days following administration.

Although continued illicit use of LSD has stimulated efforts to develop effective analytical methods for the detection of the drug and its metabolites in body fluids from suspected LSD users, the methods currently available are complicated, time-consuming, expensive to perform and plagued by other problems. These methods include high performance liquid chromatography (HPLC), gas chromatography/mass spectrometry (GC/MS) and radioimmunoassay. One problem faced by laboratories involved in the determination of LSD is the strong tendency for LSD and derivatized LSD to undergo adsorptive losses when subjected to gas chromatography. This behavior often prevents detection of the drug at the sub-nanogram/milliliter concentrations normally encountered in body fluids from LSD users.

Commercial RIAs for LSD are available from several sources, including ABUSCREEN LSD assay (® Roche Diagnostics Systems, Nutley, N.J.) and COAT-A-COUNT LSD assay (® Diagnostic Products Corp., Los Angeles, Calif.), and these products serve as a useful and relatively inexpensive method of screening for the presence of the drug. However, RIAs are not totally specific for LSD, so that an RIA-positive specimen still has to be confirmed by a second and more specific assay if the results of the analysis could have punitive consequences. The manufacturers' recommended cut-off concentration for considering a sample positive for LSD is 0.5 ng/ml, although lower cut-offs have been used in investigations where legal consequences were not a concern. The actual concentration of LSD in RIA-positive urine specimens is generally lower than that indicated by the RIA, and often considerably lower. Presumably the higher concentrations indicated by RIA are due to the cross-reactivity of LSD metabolites to the RIA antisera, but this conclusion cannot be substantiated until the major LSD metabolites in urine have been identified and their cross-reactivities determined.

In testing for other drugs of abuse, immunoassays, particularly competitive binding immunoassays, have proven to be especially advantageous. In competitive binding immunoassays, an analyte in a biological sample competes with a labeled reagent, or analyte analog, or tracer, for a limited number of receptor binding sites on antibodies specific for the analyte and analyte analog. Enzymes such as β-galactosidase and peroxidase, fluorescent molecules such as fluorescent compounds, and adioactive compounds such as $^{125}I$ are common labeling substances used as tracers. The concentration of analyte in the sample determines the amount of analyte analog which will bind to the antibody. The amount of analyte analog that will bind is inversely proportional to the concentration of analyte in the sample, because the analyte and the analyte analog each bind to the antibody in proportion to their respective concentrations. The amount of free or bound analyte analog can then be determined by methods appropriate to the particular label being used.

One type of competitive binding immunoassay is based upon the reassociation of enzyymatically inactive polypeptide fragments to form active enzyme as a step of generating a detectable signal utilized to determine the amount of analyte present in a sample. This type of assay, known as cloned enzyme donor immunoassay (CEDIA), is described in U.S. Pat. No. 4,708,929. In particular, a β-galactosidase enzyme donor polypeptide combines with a β-galactosidase enzyme acceptor polypeptide to form active β-galactosidase enzyme. Conjugating a hapten, or a small analyte or an analyte analog, to the enzyme donor polypeptide at certain sites does not affect the ability to form active β-galactosidase by a complementation reaction and hence does not affect the rate of β-galactosidase activity when in the presence of a substrate for β-galactosidase. However, when the enzyme donor-hapten conjugate is bound by anti-analyte antibody, the complementation rate is impeded, and thereby the enzyme-catalyzed reaction rate during the initial phase of the reaction is reduced. This reduction in enzyme catalyzed reaction rate can be monitored and has been used successfully to determine a plurality of analytes using the principle of competitive inhibition whereby enzyme donor-analyte conjugate present in a reaction mixture and analyte present in a sample compete for anti-analyte antibody prior to the addition of enzyme acceptor. The complementation rate of β-galactosidase formation, and hence enzyme-catalyzed reaction rate, is increased as the amount of analyte present in the sample is increased.

For the development of non-isotopic immunoassays which detect LSD and LSD metabolites, defined hapten derivatives are needed for preparation of immunogens and labeled conjugates. In particular, hapten derivatives at the 1-position of the lysergamide moiety are desirable because generally accepted strategy for preparing immunogens involves attachment of a hapten to the carrier substance at a position that is distant from the site in the molecule where immuno-specificity is desired, i.e., a site on the other side of the molecule from the ethyl side chains at the 8-position.

The preparation of antibodies to LSD for use in immunoassays to determine the drug has been accomplished in the prior art by several different approaches. One approach has been to couple the carboxyl group of lysergic acid directly to an immunogenic carrier protein, i.e. poly(L-lysine) or human serum albumin using carbodiimides. See Van Vunakis, *Proc. Nat. Acad. Sci.,* 68:1483–87 (1971); Loeffler, *J. Pharm. Sci.* 62:1817–20 (1973); and Voss, *Psychopharmacologia* 26:140–45 (1972). This approach was used in developing early RIA methods for LSD determination, but the antibodies that were produced were characterized by poor specificity for LSD and high cross-reactivities with other ergot alkaloids.

A second approach has been to couple LSD to an immunogenic carrier protein via one of the ethyl side chains at the 8-position. See Ratcliffe, *Clin. Chem.* 23:169–74 (1977). In another approach, bis-diazo benzidine was used to couple the carrier proteins via an aromatic substitution. See Luderer, *Bull. New Jersey Acad. Sci.* 19:8–10 (1974).

Finally, LSD has been coupled to an immunogenic carrier protein via a linker arm using a reaction between LSD, formaldehyde and bovine serum albumin. See Castro, *Res. Commun. Chem. Pathol. Pharmacol.* 6:879–86 (1973); Taunton-Rigby, *Science* 181:165–6 (1973); and Ratcliffe, *Clin. Chem.* 23:169–74 (1977). These authors reported the reaction to be a Mannich aminoalkylation reaction, the product of which they postulated to be substituted at the N-1, or indole nitrogen, position. More recent investigation, however, based upon known condensation reactions of indole groups with an aldehyde, suggests that the 2-position was more probably the actual site of reaction. Several references describe the Mannich reaction with indole, and these references teach that no bond is formed at the N-1 position when there is an opportunity for reaction at another position on the indole molecule. When the 3-position and 2-position are both available, the site of reaction is at the 3-position, with the indole nitrogen remaining unreactive. This is described in Orchin, *The Vocabulary of Organic Chemistry,* John Wiley & Sons, N.Y., p. 385; Funiss, *Vogel's Textbook of Practical Organic Chemistry,* 4th Ed., Longman Scientific & Technical and John Wiley & Sons, N.Y., p. 813 (1978); and Mundy, *Name Reactions and Reagents in Organic Synthesis,* John Wiley & Sons, N.Y., p. 137 (1988). When the 3-position of the indole ring is blocked, however, as is the case in the LSD molecule, the reactive site involves the 2-position, with no bond being formed at the indole nitrogen, N-1. This is described in Orchin, *The Vocabulary of Organic Chemistry,* John Wiley & Sons, NY, p. 501, FIG. 13.790. Orchin describes the indole alkaloid tryptamine undergoing a Mannich condensation reaction with an aldehyde (secologanin), with the resulting substitution occurring at the 2-position on the indole group.

The LSD derivatives of the present invention are carboxyalkyl derivatives and, in contrast to prior art derivatives, are defined compositions of matter. The derivatives of the prior art are postulated to be aminoalkyl derivatives, specifically aminomethyl, but are not defined by any analytical means as to the site of substitution or the linker composition. The present invention is believed by the inventors to be the first disclosure of discreet hapten carboxyl derivatives of LSD substituted at the N-1 position.

Haptens are partial or incomplete antigens. They are protein-free substances, mostly low molecular weight substances, which are not capable of stimulating antibody formation, but which do react with antibodies. The latter are formed by coupling the hapten to a high molecular weight carrier and injecting this coupled product into humans or animals. Examples of haptens include therapeutic drugs such as digoxin and theophylline, drugs of abuse such as morphine and LSD, antibiotics such as gentamycin and vancomycin, hormones such as estrogen and progesterone, vitamins such as vitamin B12 and folic acid, thyroxin, histamine, serotonin, adrenaline and others.

A carrier, as the term is used herein, is an immunogenic substance, commonly a protein, that can join with a hapten, thereby enabling the hapten to stimulate an immune response. Carrier substances include proteins, glycoproteins, complex polysaccharides and nucleic acids that are recognized as foreign and thereby elicit an immunologic response from the host.

An enzyme acceptor (EA) is an enzymatically inactive, polypeptide fragment of β-galactosidase produced by a deletion mutant of the β-galactosidase gene which, when combined or associated with an enzyme donor, is capable of forming active β-galactosidase enzyme by the process of complementation.

An enzyme donor (ED) is an enzymatically inactive polypeptide fragment of β-galactosidase comprising a peptide sequence capable of combining or associating with an enzyme acceptor to form active β-galactosidase enzyme.

The term immunogenic as used herein refers to substances capable of producing or generating an immune response in an organism.

The term derivative refers to a chemical compound or molecule made from a parent compound or molecule by one or more chemical reactions.

As used herein, a label or tracer is an identifying tag which, when attached to a carrier substance or molecule, can be used to detect an analyte. A label may be attached to its carrier substance directly or indirectly by means of a linking of bridging moiety. Examples of labels include enzymes such as β-galactosidase and peroxidase, fluorescent compounds such as rhodamine and fluorescein isothiocyanate (FITC), luminescent compounds such as dioxetanes and luciferin, and radioactive isotopes such as $^{125}I$.

A peptide is any compound formed by the linkage of two or more amino acids by amide (peptide) bonds, usually a polymer of α-amino acids in which the a-amino group of each amino acid residue (except the $NH_2$-teraal) is linked to the α-arboxyl group of the next residue in a linear chain. The terms peptide, polypeptide and poly(amino acid) are use synonymously herein to refer to this class of compounds without restriction as to size. The largest members of this class are referred to as proteins.

A complex is a reversible association of chemical compounds or moieties held together by weak bonds or other forces, such as an enzyme-substrate complex (an association of an enzyme and one or more substrates that is the reacting moiety in an enzyme-catalyzed reaction), an antigen-antibody complex, a hapten-antibody complex, or an active enzyme complex of β-galactosidase formed by complementation of an enzyme donor and an enzyme acceptor.

SUMMARY OF THE INVENTION

The present invention provides novel hapten derivatives of the formula

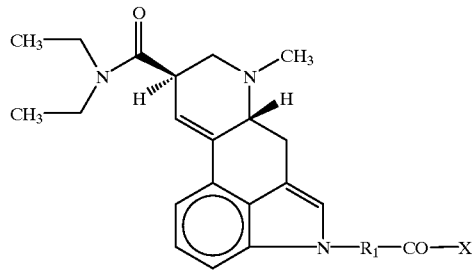

wherein $R_1$ is an alkyl, cycloalkyl or aryl group having 1 to 10 carbon atoms, preferably an alkyl group having 1 carbon atom, and wherein X is hydroxyl or

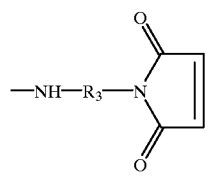

wherein $R_3$ is an alkyl, cycloalkyl or aryl group having 2 to 10 carbon atoms, preferably an alkyl group having 2 or 5 carbon atoms.

The present invention further provides novel hapten conjugates of the formula

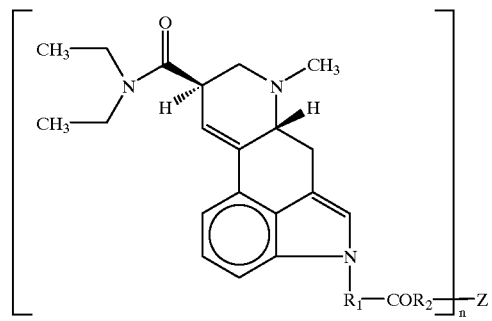

wherein $R_1$ is an alkyl, cycloalkyl or aryl group having 1 to 10 carbon atoms, wherein $R_2$ is a bond or

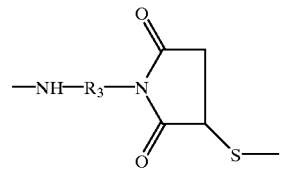

wherein $R_3$ is an alkyl, cycloalkyl or aryl group having 2 to 10 carbon atoms, preferably an alkyl group having 2 or 5 carbon atoms, Z is an immunogenic carrier substance, an enzyme donor polypeptide or a label selected from the group consisting of an enzyme, a substance having fluorescent properties and a radioactive substance, and n is from 1 to p where p is the molecular weight (MW) of Z/1000.

The present invention uniquely provides reagents for use in LSD immunoassays involving the coupling to or derivatization of the maleimide modified activated hapten precursor compound via sulfhydryl groups on an immunogenic carrier substance. The immunogens of the present invention, which include the haptenic drug covalently linked via its maleimide moiety and a sulthydryl bridge to an immunogenic carrier material, are used to stimulate the production of antibodies to LSD.

The present invention further uniquely provides reagents for use in LSD immunoassays involving the coupling to or derivatization of the N-1-carboxyalkyl hapten precursor compound via amide linkages to an immunogenic carrier substance. These immunogens of the invention, which comprise the haptenic drug covalently linked via condensation directly with amine groups on an immunogenic carrier material, are used to stimulate the production of antibodies to LSD.

In another aspect, the present invention provides immunoassay methods and reagents for the determination of LSD using the novel antibodies. The present invention also provides novel hapten-enzyme donor conjugates for particularly preferred embodiments of the assay methods. The novel conjugates are prepared from either the activated N-1-carboxyalkyl LSD analog or from the maleimide adduct of the N-1-carboxyalkyl LSD analog.

Further aspects of the invention and desirable characteristics of the reagents and assay methods will be apparent from the description that follows and the appended claims.

BRIEF DESCRIPTION OF THE DRAWINGS

The present invention will be better understood by reference to the following detailed description of the invention when considered in combination with the drawings that form part of the specification, wherein:

FIG. 7 (Lower Panels) is three graphs showing LC/MS/MS analysis of peaks treated with glucuronidase. From top to bottom, the panels show LSD-O-glucuronides 516→340; 2-oxo, 3-OH LSD 356→237; and O-LSD 340→239. Major metabolites in urine are 13-hydroxy LSD glucuronide and 14-hydroxy LSD glucuronide. The ability to detect these metabolites extends the period over which a previous exposure to LSD can be detected.

DESCRIPTION OF PREFERRED EMBODIMENTS

Figure 1:
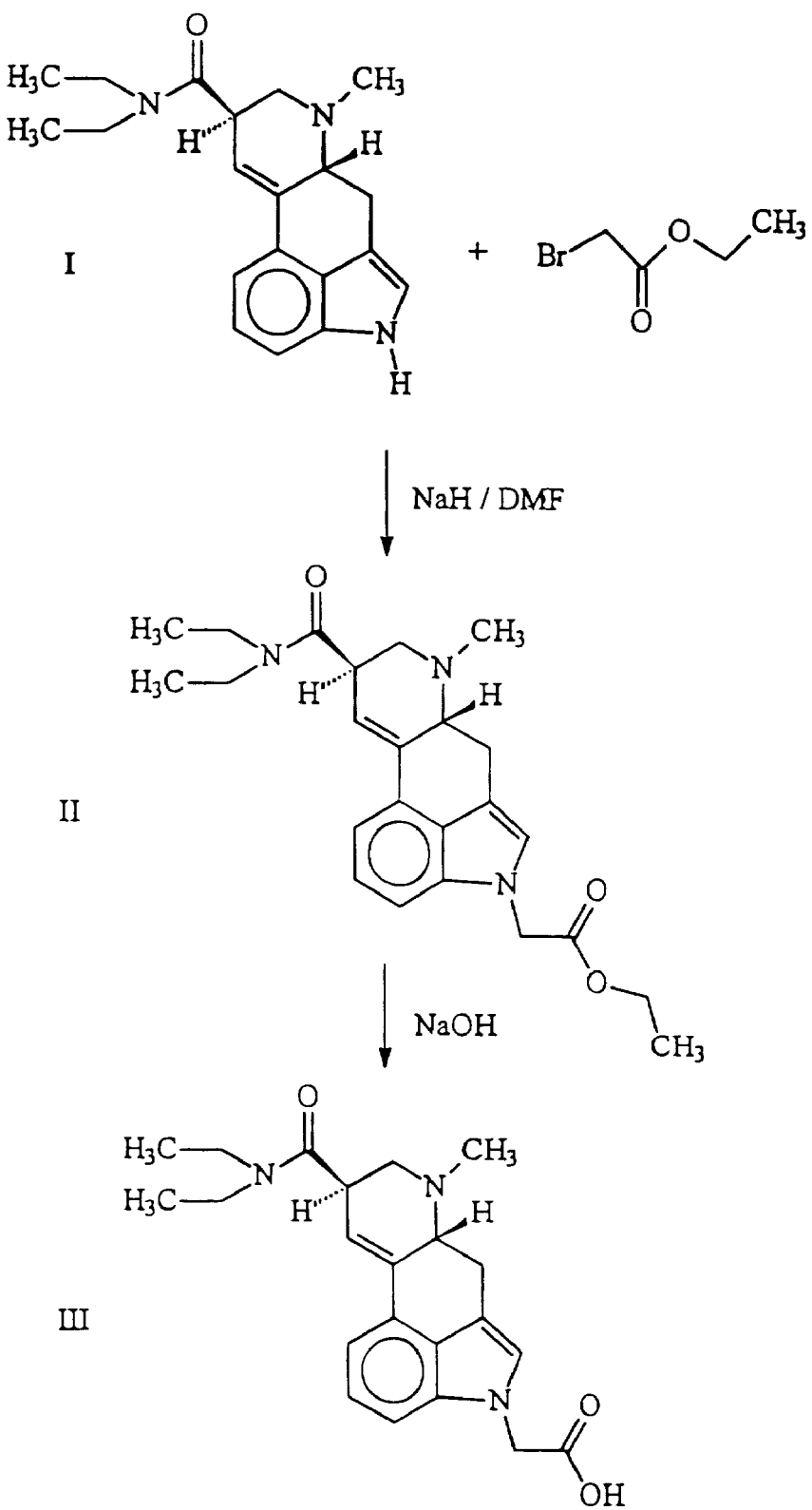
FIG. 1 illustrates a particular synthetic scheme for preparing N-1-carboxymethyl-LSD.

The present invention, in all of its interrelated embodiments, is focused on the preparation of N-1-carboxyalkyl derivative analogs of LSD which can then be used to form immunogens by coupling the derivatives to conventional immunogenic poly(amino acids) or other antigenic carrier materials and subsequently used to obtain antibodies, or the derivatives can be used to form enzyme, enzyme donor or labeled conjugates which are useful as detection reagents in immunoassays for the drugs.

The chemical structure of LSD is represented by the formula:

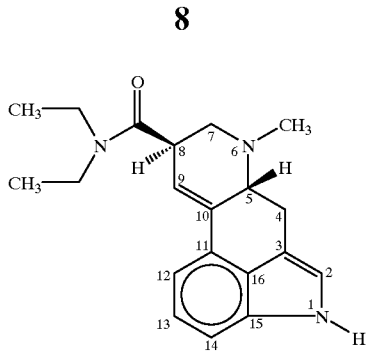

In a preferred embodiment of the present invention, N-1-caboxyalkyl derivatives of LSD are first prepared by a novel method in which N-1-alkylation is favored over N-6 alkylation, i.e. quaternization. This method involves the treatment of LSD with a molar excess of a strong base, e.g. sodium hydride, followed by addition of alkyl-haloalkylcarboxylate. Hydrolysis of the ester yields N-1-caboxyalkyl LSD. The latter derivative may be conjugated to amino groups on immunogenic carrier proteins to yield immunogens directly or may be conjugated to amino groups on linkers, i.e., maleimidoalkylamines, to give adducts suitable for conjugation to thiol groups of enzyme donor polypeptides, immunogenic carrier proteins or labeling groups.

In yet another preferred embodiment of the invention, in preparing immunogen, enzyme, or enzyme donor conjugates of the analogs, a maleimide adduct is first formed with an aminoalkyl-maleimide derivative. These aminoalkyl-maleimide derivatives are synthesized by the methods of Huber as described in PCT publication WO 90/15798 (Dec. 27, 1990). The maleimide adducts are reacted with thiol groups on the immunogen, enzyme or enzyme donor to give thioether-linked conjugates.

According to a preferred embodiment, in preparing the immunogens of the invention, a thiol-containing carrier poly(amino acid) or other substance having immunogenic properties is coupled to the maleimide hapten. Although thiolated keyhole limpet hemocyanin (KLH) is an especially preferred antigenic poly(amino acid), or carrier protein, it should be understood that various protein carriers may be employed, including albumins, serum proteins, e.g., globulins, ocular lens proteins, lipoproteins and the like. Illustrative protein carriers include bovine serum albumin, egg ovalbumin, bovine gammaglobulin, thyroxine binding globulin, etc. Alternatively, synthetic poly(amino acids) having a sufficient number of available sulfhydryl groups such as cysteine may be employed, as may other synthetic or natural polymeric materials bearing reactive functional groups. In particular, carbohydrates, yeasts, or polysaccharides may be conjugated to the hapten to produce an immunogen.

Conjugates of the activated hapten and a labeling group such as an enzyme, a substance having fluorescent properties, or a radioactive label may also be prepared and used as reagents in immunoassays. As with the immunogen and enzyme donor conjugates, the label employed must have available thiol-containing groups to be suitable for conjugation via the maleimide linker embodiment of the present invention. The thiol groups may be naturally occurring or they may be artificially introduced using a thiolating agent such as N-succinimidyl-3-(acetylthio) propionate (SATP) or 2-iminothiolane.

In order to generate antibodies, the immunogen is conveniently prepared for injection into a host animal by rehydrating lyophilized immunogen to form a solution or suspension of the immunogen. The immunogen solution is then combined with an adjuvant such as Freund's. The immunogen may be administered in a variety of sites, at several doses, one or more times, over many weeks.

Preparation of polyclonal antibodies using the immunogen may follow any of the conventional techniques known to those skilled in the art. Commonly, a host animal such as a rabbit, goat, mouse, guinea pig, or horse is injected with the immunogen mixture. Further injections are made, with serum being assessed for antibody titer until it is determined that optimal titer has been reached. The host animal is then bled to yield a suitable volume of specific antiserum. Where desirable, purification steps may be taken to remove undesired material such as nonspecific antibodies before the antiserum is considered suitable for use in performing assays.

Monoclonal antibodies may be obtained by hybridizing mouse lymphocytes, immunized as described above, and myeloma cells using a polyethylene glycol method such as the technique described in *Methods in Enzymology* 73 (Part B), pp. 314–46 (1981).

EXAMPLE 1

Thiolation of KLH

A solution of keyhole limpet hemocyanin (KLH) (12.3 mg, 12.3 nmoles) was reconstituted in 50 mM phosphate buffer (2.5 ml), pH 7.6. To this was added 2-iminothiolane hydrochloride (2-IT) (3.4 mg, 24.6 nmole). The solution was vortexed and allowed to stand at ambient temperature for 60 minutes. The thiolated KLH (KLH-SH) was desalted with 50 mM phosphate buffer (3.5 ml), pH 7.0, over a PD-10 prepacked SEPHADEX G-25 ion exchange column (® Pharmacia, Inc.) pre-equilibrated with 50 mM phosphate buffer, pH 7.6, to remove excess, unreacted 2-IT.

EXAMPLE 2

Preparation of N-1-carboxymethyl-LSD

N-1-(ethyl-carboxymethyl)-LSD (formula II) was prepared as a starting material by treating LSD (formula I) with a molar excess of sodium hydride followed by the addition of ethylbromoacetate. The ester formed was hydrolyzed to yield N-1-carboxymethyl-LSD (N-1-CM-LSD, formula III). The synthetic scheme, described in detail below, is illustrated in FIG. 1.

Because LSD was found to be difficult and hazardous to weigh by transfer due to static charge effects, a method for reconstituting a total vial and weighing by subtraction was adopted. Working in a glove box which had been purged with nitrogen gas, 7.4 mg (308 μmol) sodium hydride was weighed directly into a tared 2.5 ml conical reaction vial. Dimethylformamide (DMF), 400 μl, was added to the reaction vial, along with a magnetic stir bar, open cap, and septum with TEFLON (synthetic resin polymer)-coated face. The vial was placed in a beaker containing crushed dry ice for approximately 10 min. DMF, 300 μl, was added to a tared, 50 mg vial of LSD, and the vial was capped and inverted several times until a complete solution was obtained. The LSD solution was transferred to a small culture tube (12×75 mm), capped and placed in the dry ice for approximately 10 min. The empty LSD vial was then rinsed with acetone, dried and weighed to obtain the net weight of LSD removed by subtraction, 50 mg (154 μmol). After removing the reaction vial from the dry ice and placing on a magnetic stir plate, the LSD solution was injected while vigorously stirring the sodium hydride suspension in the vial. Evolution of hydrogen gas and bright yellow coloration was noted. The suspension was allowed to warm with stirring for about 5 min, at which point the gas evolution had subsided. Ethylbromoacetate, 17 μl (164 μmol), was then injected and stirred for approximately 2 minutes. After removing the vial from the glove box, a 1–2 μl aliquot was removed for HPLC analysis, and the vial was then placed in a −70° C. freezer while the HPLC was being run. The HPLC aliquot was diluted in a 12×75 mm culture tube with 20 μl acetonitrile and 20 μl of 0.1M triethylamine acetate (TEA-Ac). The sample was injected on a C4 analytical column (Vydac) and the following program was run: 0–5 mn, 100% 0.1M TEA-Ac (pH 7); 5–55 min, 0–50% acetonitrile/0.1M TEA-Ac; 55–60 min, 100% acetonitrile; 60–70 min, 100% 0.1M TEA-Ac. The flow rate was 1 ml/min, with UV detection at 320 and 280 nm. The HPLC showed nearly complete conversion of LSD eluting around 30–32% acetonitrile to a major product eluting around 40–42% acetonitrile which showed a slight back shoulder. The N-6 quatetnized side-product elutes right after LSD, i.e., 32–33% acetonitrile.

The product was isolated by preparative HPLC on a 2.2×25 cm C4 column using the following program: 0–10 min, 10% acetonitrile/0.1M TEA-Ac; 10–160 min, 10–60% acetonitrile/0.1M TEA-Ac; 60–65 min, 65% acetonitrile/ 0.1M TEA-Ac; 65–75 min, 10% acetonitrile/0.1M TEA-Ac. The flow rate was 8 ml/min. The load solution was prepared by diluting the cold reaction mixture with 1 ml 0.1M TEA-Ac, filtering the resultant, slightly turbid solution through a 1 μm syringe filter, and injecting the clear filtrate, 1.8 ml, on a 2 ml loop. The desired product eluted toward the end of the gradient with a back shoulder. Fractions were collected manually over the major peak, taking care to change fractions at the back shoulder. This back shoulder corresponds to partially resolved N-1-(ethyl-carboxymethyl)-isoLSD, i.e. epimerized at the 8-position. Analytical HPLC was performed on the major fractions and those which were free of the isoLSD shoulder were pooled and lyophilized. The fraction was analyzed by 1 H-NMR in acetonitrile-$d_3$ and identity confirmed by mass spectrometry (MS). The NMR spectrum of N-1-(ethyl-carboxymethyl)-LSD showed an absence of the LSD 1-position NH at 9.0 ppm. However, all other LSD resonances were seen at approximately the same position as in the parent drug. This strongly indicated that the 1-position was substituted. In addition, new resonances were noted for the carboxymethyl $CH_2$ (4.9 ppm, 2 proton singlet) and the ethyl ester ($CH_2$ at 4.2 ppm, 2 proton quartet, and $CH_3$ at 1.3 ppm, triplet overlapped with diethylamide resonances). The recovered yield was calculated by comparing UV/visible in acetonitrile/water (50:50) using MW=409.5 and $E_{max}$=5895 for the peak around 320 nm and found to be 30 mg.

N-1-(ethyl-carboxymethyl)-LSD starting material (28.5 mg, 70 μmol) was dissolved in 3.5 ml of ethanol and transferred to a small vial equipped with a septum/needle attached to an inert gas line and small stir bar. The reaction vial was purged with argon gas. Sodium hydroxide, 75 μl of a 1N solution, was then injected with stirring. The reaction was monitored using the analytical system described above for preparing the starting material. The product eluted at about 24–25% acetonitrile as a sharp peak. A small amount of isoLSD derivative side product was noted which appeared as a back shoulder on the major peak. The reaction was complete in approximately 2 hr. The reaction mixture was then neutralized by adding one equivalent of acetic acid and 1 ml of water, and the resulting solution was clear. The product was isolated and desalted by HPLC on a preparative C4 column using 20 mM TEA-Ac, pH 7, and acetonitrile according to the following program: 0–5 min, 0% acetonitrile/20 mM TEA-Ac; 5–55 min, 0–50% acetonitrile/ 20 mM TEA-Ac; 55–60 min, 100% acetonitrile. The flow rate was 8 ml/min. The major peak, which eluted around 28–29% acetonitrile, was collected and fractions changed on the back side of the peak to eliminate any shoulder for isoLSD derivative. The pooled fractions were lyophilized and re-lyophilized 2 times from water/acetonitrile 4:1 to get ride of the TEA-Ac and convert the product to a zwitterion. The product was analyzed by 1 H NMR in a mixture of acetonitrile-$d_3$ and deuterium oxide. The ethyl ester resonances noted above were confirmed to absent in the NMR whereas the other resonances as noted above were intact. The product was also analyzed by MS and confirmed to have a molecular ion peak corresponding to the theory molecular weight (MW) of 381. The recovered yield was calculated by UV in acetonitrile-H20 as described above for the staring material using MW=381 and $E_{max}$=5895. The yield of N-1-CM-LSD was found to be between 20 mg.

EXAMPLE 3

Preparation of N-1-(carboxymethyl)-LSD N-hydroxysuccinimide ester)

Figure 2:
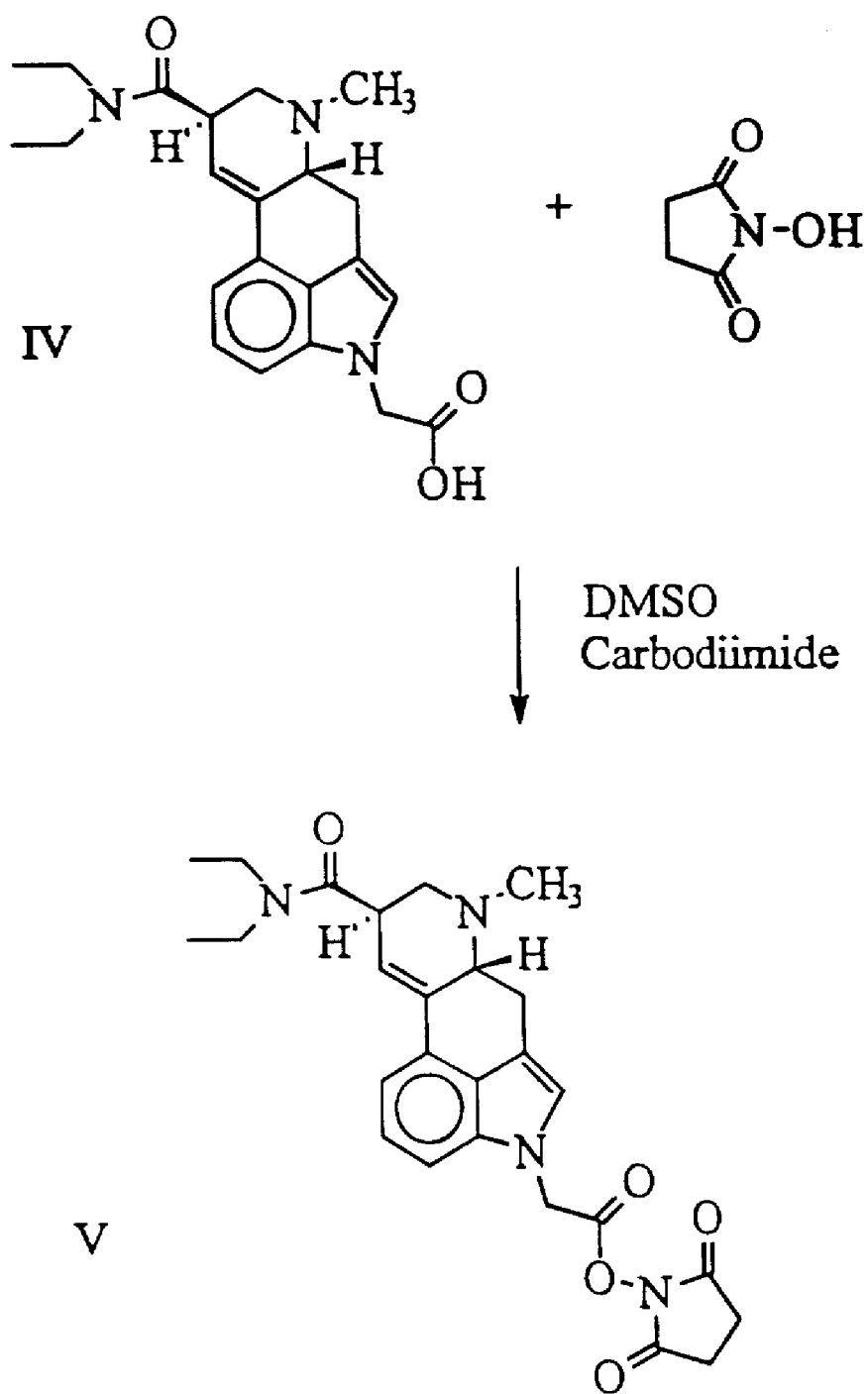
FIG. 2 illustrates a particular synthetic scheme for preparing the N-hydroxysuccinimide ester of N-1-carboxymethyl-LSD.

As illustrated in FIG. 2, N-1-(carboxymethyl) LSD N-hydroxysuccinimide ester (N-1-CM-LSD-NHS, formula V) was prepared by dissolving a sample of N-1-carboxymethyl-LSD (6.6 mg, 17.3 µmoles, formula IV) in 1.0 ml dimethylsulfoxide (DMSO). To that solution N-hydroxysuccinimide (NHS) (14 mg, 121 µmoles) and 1-ethyl-3-(3-dimethylaminopropyl)carbodiimide hydrochloride (EDC) (23.2 mg, 121 µmoles) was added. The solution was vortexed and incubated at ambient temperature overnight. The activated N-1 -CM-LSD-NHS (Formula V) was used in Examples 4 and 5 without any purification.

EXAMPLE 4

Conjugation of N-1-carboxymethyl)-LSD N-hydroxysuccinimide ester to KLH

A solution of KLH (15.0 mg, 15 nmoles) in 4.0 ml phosphate buffer was added to a solution of N-1-CM-LSD-NHS (5.7 mg, 15.0 µmoles) in 1.0 ml DMSO, prepared as in Example 3. The resulting solution was vortexed gently for two minutes and allowed to stand at ambient temperature for 8.0 hours. The immunogen [N-1-CM-LSD]$_n$-KLH was dialyzed against water/MeOH (80:20 v/v) for three days. The immunogen was then freeze-dried to form a lyophilized powder material. Loading of the immunogen, calculated as described in Example 7 below, was determined to be approximately 199, using an extinction coefficient of 17,060 $M^{-1}$ $cm^{-1}$ at 250 nm for N-1-CM-LSD.

EXAMPLE 5

Preparation of N-1-(maleimidoethylamino-carbonylmethyl)-LSD

Figure 3:
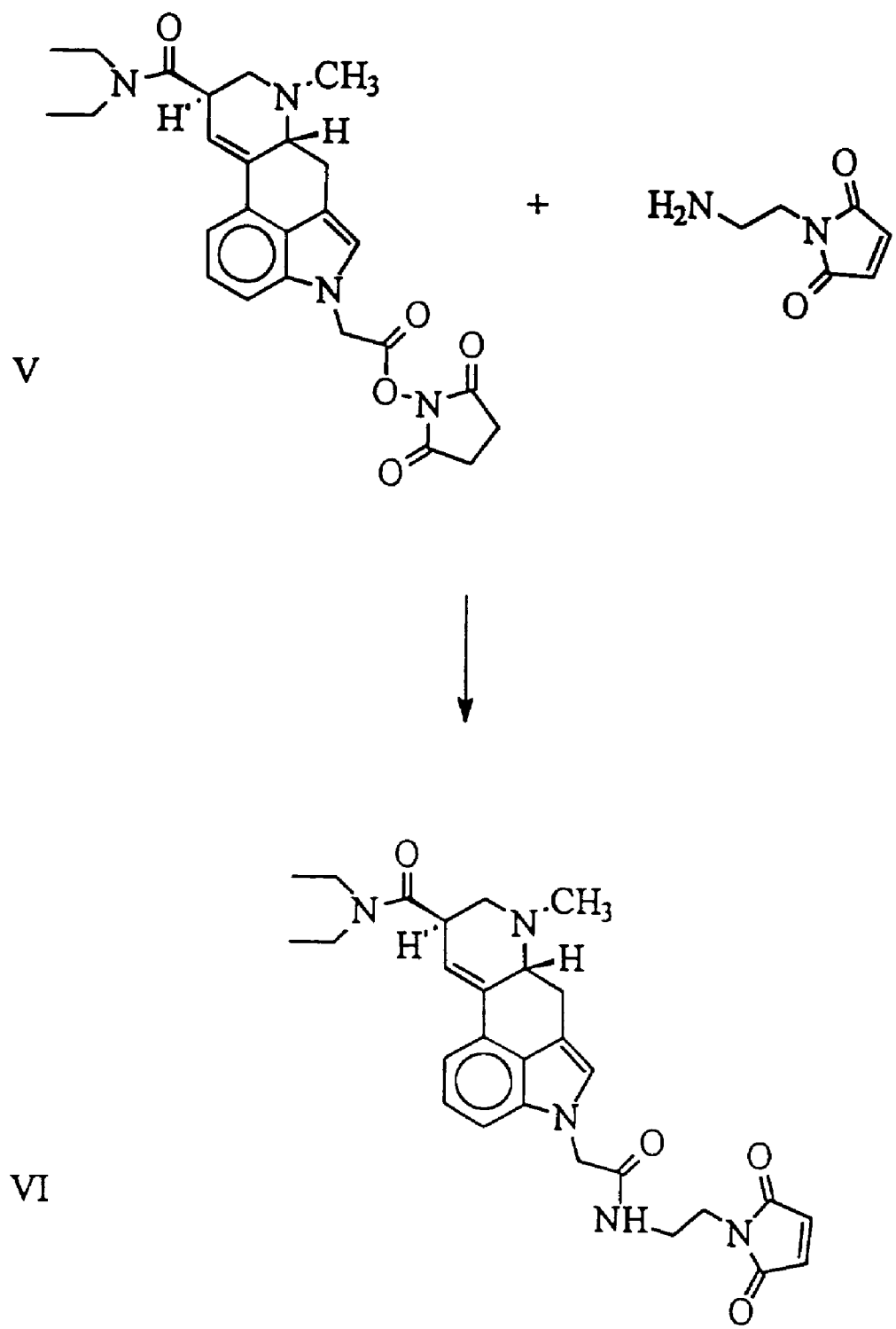
FIG. 3 illustrates a particular synthetic scheme for preparing N-1-(maleimidoethylamino-carbonylmethyl)-LSD.

As illustrated in FIG. 3, a 2-fold excess of maleimidoethylamine hydrochloride (MEA HCl, formula V, 6.1 mg, 34.6 µmoles) in 1.5 ml phosphate buffer was added to the activated N-1-CM-LSD-NHS from Example 3 (6.6 mg, 17.3 µmoles). MEA HCl was synthesized by the method of Huber as described in PCT publication WO 90/15798 (Dec. 27, 1990). The progress of the reaction was monitored by HPLC. The N-1-(maleimidoethylamino-carbonylmethyl)-LSD (N-1-MEA-CM-LSD, formula VI) was then purified by HPLC.

EXAMPLE 6

Conjugation of N-1-(maleimidoethylamino-carbonylmethyl)-LSD to KLH

KLH-SH solution (7.0 mg, 7.0 µmoles) in 2.1 ml of phosphate buffer from Example 1 was added to a solution of N-1-MEA-CM-LSD (3.5 mg, 7.0 mmoles) in DMSO (0.60 ml). The resulting solution was vortexed gently for two minutes and allowed to stand at ambient temperature for 5 hours. The protein conjugate [N-1-MEA-CM-LSD]$_n$-KLH was dialyzed against $H_2O$:MeOH (80:20 v/v) for three days, then freeze-dried to form a lyophilized powdered material.

The number of N-1-MEA-CM-LSD adducts incorporated into the protein carrier KLH (loading of immunogen) was determined as follows: One milligram of [N-1-MEA-CM-LSD]$_n$-KLH was dissolved in 1.0 ml of 1.0N NaOH. The spectrum of the solution was recorded between 200 and 400 nm against the same solvent as reference. Using the extinction coefficient of 5,899 $M^{-1}$ $cm^{-1}$ at 320 nm for N-1-MEA-CM-LSD in which there is no absorption for KLH, the molar ratio was calculated to be 226:1.

EXAMPLE 7

Preparation of N-1-(maleimidopentylamino-carbonylmethyl)-LSD:ED Conjugate

N-1-(maleimidopentylamino-arbonylmethyl)-LSD (N-1-MEA-CM-LSD) was first prepared. To a solution of N-1-CM-LSD-NHS (50.11 mg, 131.4 µmoles) prepared as described in Example 3, an approximately equivalent number of moles of maleimidopentylamine hydrochloride (MPA) (28.78 mg, 131.6 µmoles) in dimethylformamide (DMF) was added. To keep the reaction mixture at neutral pH, 300 µl of triethylamine (TEA) was added and the pH checked. The progress of the reaction was monitored by HPLC. The N-1-MPA-CM-LSD was then HPLC purified and used in the preparation of the ED conjugate.

A solution of thiolated ED28 (5.0 mg, 0.5 µmoles) was prepared and desalted in 3.5 ml phosphate buffer. This solution was then added to the solution of N-1-MPA-CM-LSD (1.67 mg/1.5 ml DMF. The resulting mixture was vortexed gently for 2 minutes and allowed to stand at ambient temperature for 55 minutes. The protein conjugate N-1-MPA-CM-LSD:ED was HPLC purified using a Vydac semipreparative C4 column.

EXAMPLE 8

Preparation of Monoclonal Antibodies

Preparation of the immunogen and immunization of the host animal were accomplished using techniques which will be well known to those skilled in the art. Each of the immunogens prepared in Examples 4 and 6 were administered to mice in a series of injections. Hybridoma cell lines were then developed from fusions using immunized spleens. Supernatant antibody was evaluated as described below, and ascites was produced from useful clones. Ascites was then purified, yielding monoclonal antibody. All of the biological and purification methods were performed in a manner well known to those skilled in the art In this example, supernatant antibodies were selected from 96-well culture plates using a CEDIA homogeneous assay. As previously described, the CEDIA assay utilizes two genetically engineered, enzymatically inactive fragments of β-galactosidase. The smaller polypeptide, the enzyme donor, can recombine spontaneously, with the larger fragment, the enzyme acceptor, to form active β-galactosidase, in a process called complementation. When a specific antibody to the ligand or analyte attaches to the enzyme donor conjugate, complementation is inhibited. The addition of free ligand to this system will modulate the inhibition of complementation. This assay principle was used to screen fusion products in a 96-well format.

A primary screening of the fusion products was first performed to evaluate the ability of the antibodies to bind to the enzyme donor conjugate prepared in Example 8 and to inhibit complementation. The number of inhibition-positive clones were then narrowed further by performing a secondary screening assay to determine whether the free drug would modulate or compete with the enzyme donor conjugate for the antibody. The modulation assay also identified specific clones when screened against cross-reacting analytes. The clones which modulated with the specific analytes of choice were then grown for further study. The culture supernatants containing the monoclonal antibodies were collected and evaluated on the HITACHI 717 analyzer (® Boebringer Mannheim Corp., Indianapolis, Ind.) as described in Example 9 below.

EXAMPLE 9

Assay for LSD

A CEDIA assay for LSD was performed using the enzyme donor conjugate prepared in Example 7 and the antibody produced according to Example 4.

A preferred assay method comprises the steps of:

(a) contacting the sample with:
  (i) an enzyme donor polypeptide conjugate, preferably having the structure

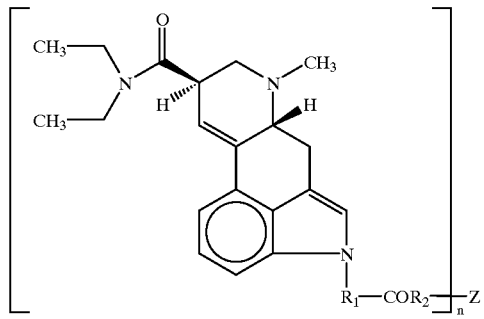

wherein Z is an enzyme donor polypeptide of beta-galactosidase;
  (ii) an enzyme acceptor polypeptide wherein said enzyme acceptor polypeptide is characterized by forming with said enzyme donor polypeptide conjugate an active enzyme complex having beta-galactosidase activity in the absence of an antibody to LSD;
  (iii) an antibody specific for LSD, preferably raised against the structure

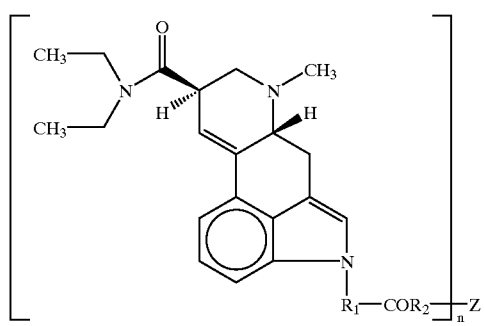

wherein Z is an immunogenic carrier substance; wherein said enzyme donor conjugate is capable of competitively binding to said antibody, thereby inhibiting the formation of active enzyme complex; and
  (iv) a substrate capable of reacting with said active enzyme complex, such that the rate of conversion of said substrate by said active enzyme complex can be monitored; and
(b) measuring the rate of conversion of said substrate by said active enzyme complex as a measure of the amount of LSD in said sample.

The following reagents are prepared:

| Antibody reagent: | |
| --- | --- |
| Antibody | 57 ng/ml |
| PIPES (piperazine-N,N-bis-[2-ethanesulfonic acid]) | 100 mM |
| NaCl | 500 mM |
| Fetal bovine serum | 0.5% |
| EGTA | 10 mM |
| Magnesium acetate | 10 mM |
| Sodium azide | 20 mM |
| pH | 6.90 |

| Donor reagent: | |
| --- | --- |
| Enzyme donor conjugate | 0.487 nM |
| CPRG (chlorphenylred-β-D-galactopyranoside) | 3 mg/ml |
| PIPES | 100 mM |
| NaCl | 400 mM |
| EGTA | 10 mM |
| Fragmented BSA | 2 mg/ml |
| Sodium azide | 20 mM |
| pH | 6.90 |

| Acceptor reagent: | |
| --- | --- |
| Enzyme acceptor | 880 U/ml |
| Magnesium acetate | 10 mM |
| NaCl | 400 mM |
| PIPES | 100 mM |
| EGTA | 10 mM |
| Sodium azide | 20 mM |
| pH | 6.90 |

Figure 4A:
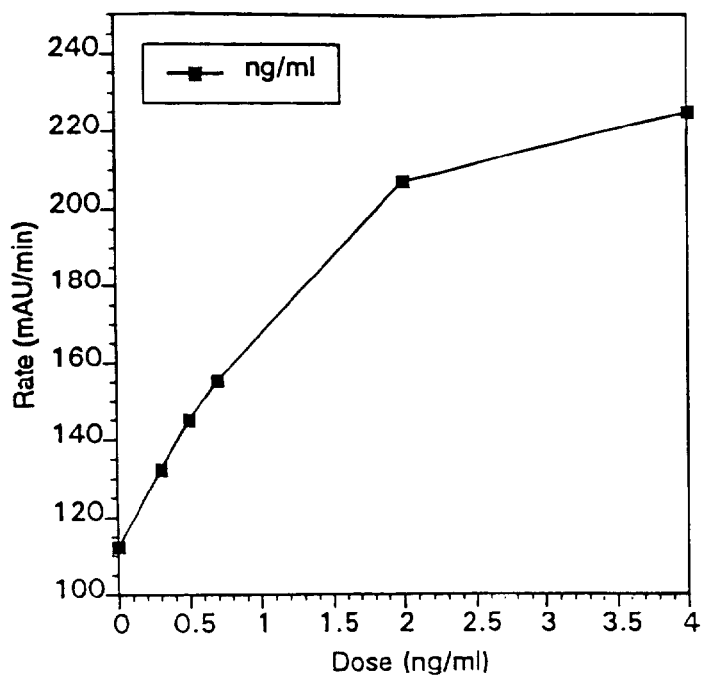
FIGS. 4(a) and 4(b) are graphs showing dose response curves at varying levels of LSD using enzyme donor conjugates and antibodies of the present invention.

Assays were performed using an HITACHI 911 analyzer. The instrument dispensed 12 μl of sample containing LSD, and 100 μl of antibody reagent was added. The mixture was allowed to incubate at 37° C. for 60 seconds, after which 100 μl of donor reagent was added and allowed to incubate for 530 seconds. Finally 140 μl of the acceptor reagent was added. The absorbance rate was measured over the time period of 295 sec to 375 sec following the addition of the acceptor reagent. The primary wavelength used was 570 nm, with 660 nm used as the secondary wavelength. The absorbance rate at 570 nm was plotted against LSD concentration to construct the dose response curve shown in FIG. 4(a). The results obtained with an LSD specific monoclonal antibody raised against the immunogen of Example 4 are as follows:

| Dose, ng/ml | Rate, mAU/min |
|---|---|
| 0.0 | 112.4 |
| 0.3 | 132.2 |
| 0.5 | 145.0 |
| 0.7 | 155.3 |
| 2.0 | 207.0 |
| 4.0 | 224.8 |
| 100 | 228.7 |

EXAMPLE 10

Assay for LSD

In a similar manner to that described in Example 9, a CEDIA assay for LSD was performed using the enzyme donor conjugate prepared in Example 7 and an LSD specific monoclonal antibody raised against the immunogen of Example 6. The results obtained are as follows:

| Dose, ng/ml | Rate, mAU/min |
|---|---|
| 0.0 | 63.6 |
| 0.3 | 67.6 |
| 0.5 | 69.9 |
| 0.8 | 72.6 |
| 1.6 | 80.8 |
| 4.0 | 107.4 |

Figure 4B:
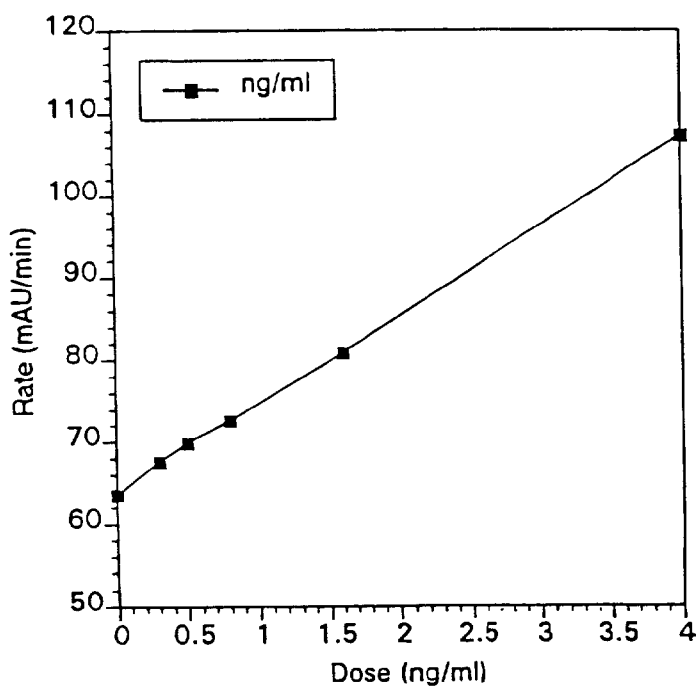

The response curve obtained by plotting the LSD dose against the rate is shown in FIG. 4(b).

It is readily appreciated from the data in this Example and in Example 9 that antibodies with very high affinity can be produced using either immunogenic conjugates of the type exemplified in Example 4 or those exemplified in Example 6. Antibodies raised against either conjugate are produced that bind LSD-enzyme donor conjugates in a manner that is detectably inhibitable at an LSD dose of 0.3 ng/mL, and inhibitable at about the 50% maximum level at an LSD dose of about 1 ng/mL. By calculating the effective concentration of each of the assay components at a time when the LSD, conjugate, and antibody are interacting, it is apparent that the affinity of the antibodies for LSD used in these examples is at least about $10^{10}$ $M^{-1}$. More generally, antibodies of an affinity of only $10^9$ $M^{-1}$ can be used in assays of this type. For an assay of good sensitivity in the range of interest, affinities of at least about $10^{10}$ $M^{-1}$ are preferred, and affinities of at least about $10^{10}$ $M^{-1}$ are even more preferred.

EXAMPLE 11

Cross-reactivity testing

Using the methods outlined, monoclonal antibodies were identified that had a modulation in the CEDIA (LSD dose of 0.5 ng/mL) of up to about 24%. Antibodies with modulations between 12–24% were subjected to further testing. Different antibody clones had different cross-reactivity profiles for potential interfering substances. Cross-reactivity was tested by spiking various potential cross-reactants into human urine containing a preservative.

Tables 1 and 2 show the cross reactivity data for one monoclonal antibody with the laboratory designation 19A7. This antibody has a modulation with LSD of 16%.

TABLE 1

Percent cross-reactivity is expressed as:
$$100 \times \frac{\text{Observed Dose}}{\text{Concentration of Cross-reactant Added}}$$

| Compound | Concentration Added (ng/mL) | Concentration Observed (ng/mL) | % Cross-Reactivity |
|---|---|---|---|
| d-LSD | 0.5 | 0.5 | 100.00 |
| Alpha Ergotryptine | 500,000 | 0.25 | 0.00000 |
| Dihydroergotamine | 125,000 | <0.01 | 0.00005 |
| d-LAMPA | 0.5 | 0.29 | 58.7 |
| Ecogonine | 100,000 | <0.01 | 0.00000 |
| Ecogonine Methyl Ester | 100,000 | <0.01 | 0.00000 |
| Ergonovine | 10,000 | 0.58 | 0.00700 |
| Ergotamine | 100,000 | <0.01 | 0.00000 |
| Iso LSD | 2,500 | 0.93 | 0.04000 |
| Lysergic Acid | 100,000 | <0.01 | 0.00000 |
| Lysergol | 5,000 | 0.01 | 0.00034 |
| Methysergide Maleate | 50,000 | 0.74 | 0.00147 |
| Psilocybin | 10,000 | <0.01 | 0.00000 |
| Psilocyn | 10,000 | <0.01 | 0.00000 |
| Seretonine | 1,000,000 | <0.01 | 0.00000 |
| Tryptophan | 100,000 | <0.01 | 0.00000 |
| 2oxo-3hydroxy LSD | 30 | 0.55 | 1.82 |

TABLE 2

| Compound | Concentration Added (ng/mL) | Concentration Observed (ng/mL) | % Cross-Reactivity |
|---|---|---|---|
| Acetaminophen | 500000 | 0.0 | <0.00001 |
| Acetylsalicylic Acid | 500000 | 0.0 | <0.00001 |
| Amoxicillin | 100000 | 0.0 | <0.00001 |
| Amphetamine | 500000 | 0.0 | <0.00001 |
| Benzoylecgonine | 500000 | 0.0 | <0.00001 |
| Captopril | 500000 | 0.0 | <0.00001 |
| Chlordiazepoxide | 100000 | 0.0 | <0.00001 |
| Cimetidine | 500000 | 0.0 | <0.00001 |
| Codeine | 500000 | 0.0 | <0.00001 |
| Diazepam | 500000 | 0.0 | <0.00001 |
| Digoxin | 100000 | 0.0 | <0.00001 |
| Enalapril | 500000 | 0.0 | <0.00001 |
| Fluoxetine | 400000 | 0.48 | 0.00012 |
| Ibuprofen | 500000 | 0.0 | <0.00001 |
| Levothyroxine (T4) | 50000 | 0.0 | <0.0001 |
| Methamphetamine | 200000 | 0.45 | 0.00019 |
| Morphine | 100000 | 0.0 | <0.00001 |
| Nifedipine | 500000 | 0.0 | <0.00001 |
| Phencyclidine | 500000 | 0.11 | 0.00002 |
| Phenobarbital | 500000 | 0.0 | <0.00001 |
| Ranitidine | 500000 | 0.15 | 0.00003 |
| Salicyluric acid | 500000 | 0.0 | <0.00001 |
| Secobarbital | 500000 | 0.0 | <0.00001 |
| Tolmetin | 500000 | 0.0 | <0.00001 |
| Verapamil | 500000 | 0.45 | 0.00009 |
| 11-nor-$\Delta^9$-THC-COOH | 10000 | 0.0 | <0.0001 |

As for any diagnostic test, it is desirable for an LSD assay to have selectivity for the intended analyte over potential interfering substances. Amongst substances that can interfere are naturally excreted products, excreted forms of pharmaceuticals used for treatment, and excreted forms of other substances of abuse. Structures with a resemblance to LSD are in general more likely to interfere. When designing an immunoassay for LSD, it is preferable to select an anti-LSD antibody that has a cross reactivity of less than 0.1%, preferably less than 0.01%, and still more preferably less than 0.001% for any of the substances listed in Table 1 and Table 2, except for dLAMPA or 2-oxo-3-hydroxy LSD. Also preferred are antibodies having less than 5%, preferably less than 2% cross-reactivity with 2-oxo-3-hydroxy LSD. Cross-reactivity with nor-LSD is optional. In one embodiment of this invention, the cross-reactivity with nor-LSD is at least about 20%, more typically over 30%. In another embodiment, the cross-reactivity with nor-LSD is less than about 10%, preferably less than 5%, more preferably less than 1%. Another class of potential interfering drugs is phenothiozines, exemplified by chlorpromazine. Preferably, the antibody has a cross-reactivity with such drugs of less than 1%, more preferably less than 0.1%, and still more preferably less than 0.01%. The cross-reactivities indicated in this section are also desirable properties for a plurality of assay reagents when used in a combination in the context of a particular assay system. Examples are a monoclonal or polyclonal antibody used in combination with an LSD-protein conjugate, including an LSD-enzyme conjugate or an LSD-enzyme donor conjugate. Cross-reactivities are generally more prominent in assays conducted at higher concentration, in a homogeneous system, in a shorter time period, or in a non-equilibrium situation. Reagents developed for less stringent assays are not necessarily suited for assays conducted under these conditions without further testing or development.

On the other hand, reactivity with the metabolite derivatives of LSD besides the parent compound will clearly be of benefit in the testing for LSD abuse. Putative urinary metabolites of interest include but are not limited to hydroxy-LSD-glucuronide. An additive effect of several derivatives will generally improve the sensitivity when biological samples are tested. In addition, if a particular derivative has a longer metabolic profile than LSD itself, then monitoring can continue for a longer period after the suspected dose.

EXAMPLE 12

Performance testing on clinical samples

The performance of an assay with clinical samples is affected not only by the known drugs, but also by a wide spectrum of unknown metabolites. In establishing the specificity of a diagnostic assay, it is standard practice to evaluate a large panel of samples from different subjects.

The enzyme assay for LSD described in the previous examples underwent specificity testing using urine samples known to be free of LSD. Results using two different monoclonal antibodies raised against an N-1 LSD conjugate are shown in Table 3.

TABLE 3

| RANGE ng/ml | # of Samples | % of Samples |
| --- | --- | --- |
| 19A7 Summary | | |
| −0.75 to −1.00 | 0 | 0.00% |
| −0.50 to −0.75 | 0 | 0.00% |
| −0.25 to −0.50 | 1 | 0.05% |
| −0.00 to −0.25 | 1359 | 67.54% |
| 0.00 to 0.25 | 647 | 32.17% |

TABLE 3-continued

| RANGE ng/ml | # of Samples | % of Samples |
| --- | --- | --- |
| 0.25 to 0.50 | 4 | 0.20% |
| 0.50 to 0.75 | 0 | 0.00% |
| 0.75 to 1.00 | 1 | 0.05% |
| >1.0 | 1 | 0.05% |
| Total 2012 | | |
| 10E6 Summary | | |
| −0.75 to −1.00 | 1 | 0.05% |
| −0.50 to −0.75 | 13 | 0.67% |
| −0.25 to −0.50 | 387 | 19.88% |
| −0.00 to −0.25 | 1128 | 57.94% |
| 0.00 to 0.25 | 416 | 21.37% |
| 0.25 to 0.50 | 3 | 0.15% |
| 0.50 to 0.75 | 2 | 0.10% |
| 0.75 to 1.00 | 1 | 0.05% |
| >1.0 | 1 | 0.05% |
| Total 1952 | | |

Using a cut-off level of 0.5 ng/mL, two of 2012 samples (0.1%) gave a false positive reaction for LSD when using antibody 19A7, and four of 1952 samples (0.2%) gave a false positive reaction for LSD when using antibody 10E6. Generally, a false positive rate of less than about 1% is used, with rates of less than 0.5%, 0.2%, and 0.1% being progressively more preferred.

These two antibodies were also tested against a panel of 379 samples positive for methadone, another substance of abuse. The presence of methadone in these urine samples was confirmed using an immunoassay specific for methadone. The number of false positives at a level above 0.5 ng/mL was 16 out of 379 (4%) for the 10E6 antibody and 0 out of 379 for the 19A7 antibody (<0.3%). Generally, a false positive rate with methadone-positive samples of less than 1% is desirable, with a rate below 0.3% being preferred.

EXAMPLE 13

Fractionation of a urinary metabolite recognized by an LSD antibody

An immunoaffinity extraction method was developed to purify LSD and any LSD derivatives present in urine samples from individuals administered LSD.

Monoclonal antibody 19A7 specific for LSD was attached to aldehyde-derivatized Sepharose® 4B by reductive amination. Urine samples containing LSD were incubated with affinity resin, the resin was washed, and bound drug was eluted in a small volume of methanol. Recovery of LSD added to drug-free urine was >95%, while recovery of the weakly-bound LSD metabolite, 2-oxo, 3-hydroxy LSD was 65%. Lysergic acid methyl-propyl amide (LAMPA) or deuterated LSD can be added as internal standard prior to immunoaffinity extraction on order to monitor recovery.

Samples were processed by GC/MS by evaporation of the methanol and derivatization with N, O-bis (trimethylsilyl) trfluoroacetamide (BSTFA). GC/MS analysis of the derivatized immunoassay extracts gave dramatically reduced background signal as compared with conventional solid-phase extraction. An LOD of 50 pg/mL and an LOQ of 61 pg/mL were obtained using conventional equipment (CG/MS model # BP 5971) under routine conditions.

Figure 5:
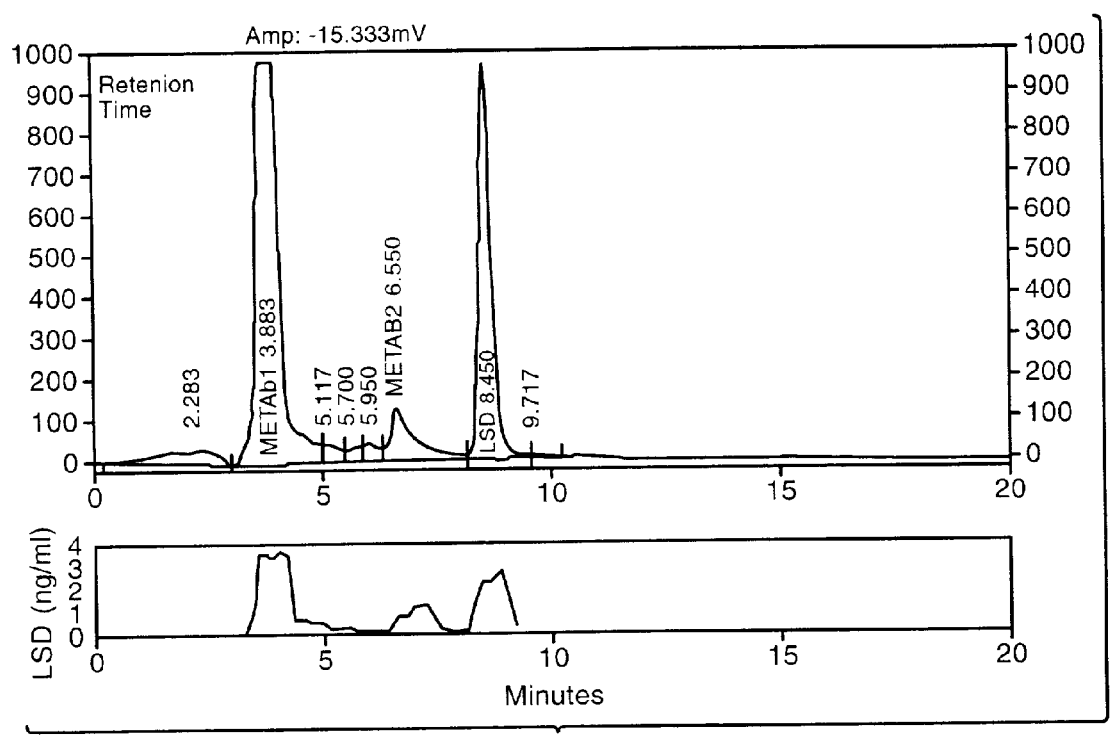
FIG. 5 is two graphs showing reverse-phase HPLC analysis of material immunopurified from urine using anti-LSD antibody. Upper panel shows total substance; lower panel shows LSD reactivity measured in the LSD enzyme immunoassay.

The immunoaffinity extraction method was also used to isolate potential urinary metabolites of LSD. Urine samples testing positive for LSD by immunoassay and GC/MS were extracted, fractionated by reverse-phase HPLC, and the fractions were analyzed by a CEDIA® assay for LSD. A number of samples contained a fluorescent immunoreactive peak (exitation at 320 nm; emission at 400 nm), eluting earlier than the parent LSD (FIG. 5). Preliminary characterization of this peak by mass spectrometry show that the metabolite has a molecular weight of 516, which corresponds to hydroxylation of LSD followed by glucuronidation. A substance of 340 molecular weight was also seen, corresponding to loss of the glucuronide. Treatment of the metabolite in the HPLC peak with *E. coli* β-glucuronidase resulted in a shift of mobility on HPLC to an elution volume between that of the original peak and parent LSD.

These observations are consistent with the hypothesis that a glucuronic acid conjugate of LSD is a principal metabolite excreted into the urine of subjects administered with LSD. The metabolite is recognized by the antibody used for affinity chromatography and in the assay.

Figure 6:
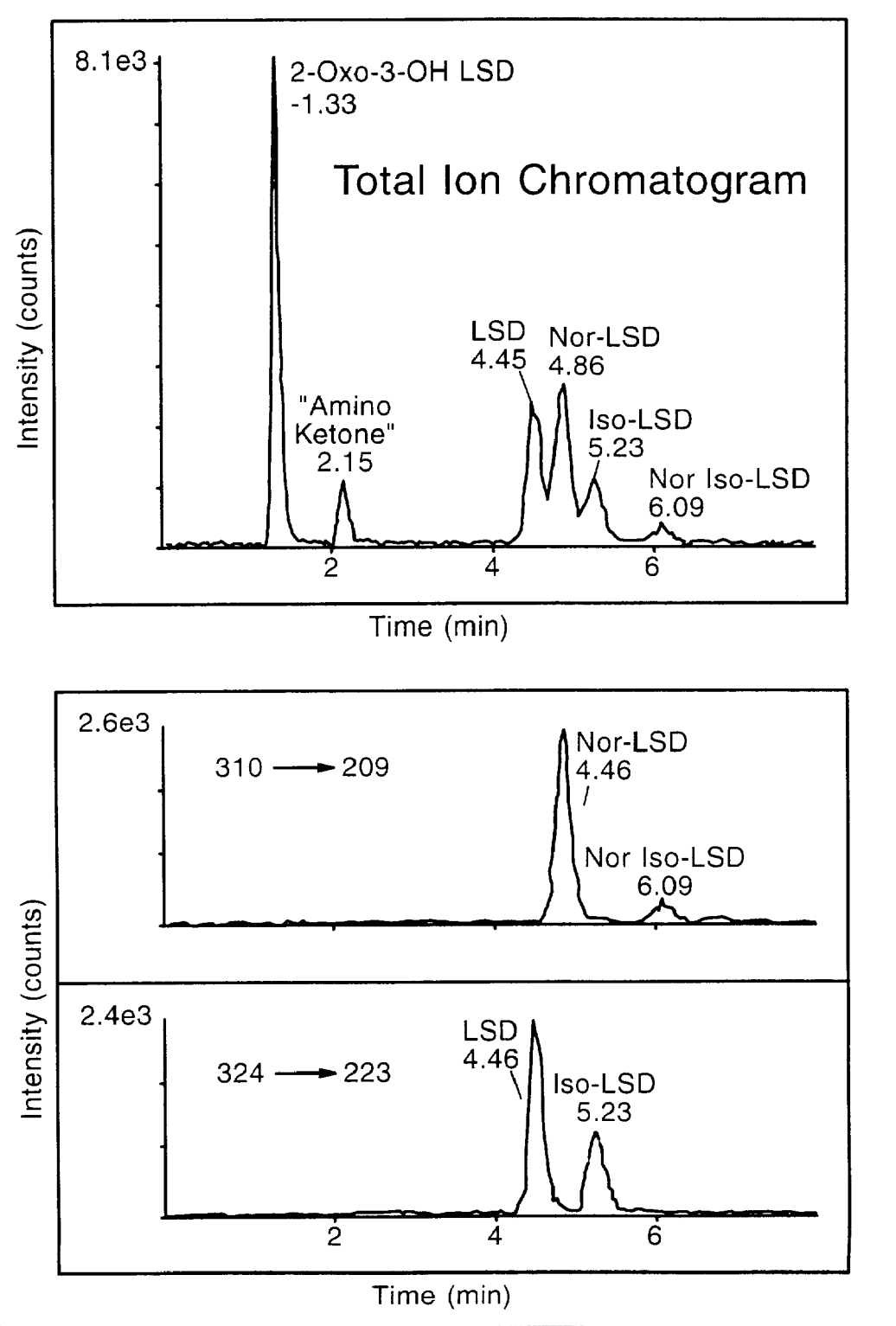
FIG. 6 is three graphs showing reverse-phase HPLC/MS/MS separation of a standard mixture of LSD related compounds. Upper panel: Total ion chromatograph; Middle panel: 310→209; Lower panel: 324→223.

Further confirmation of the identity of the metabolites was obtained by reverse-phase HPLC/MS/MS. FIG. 6 shows the separation of various LSD metabolites (2-oxo,3-hydroxy LSD, nor-LSD) and analogs (iso-LSD, nor-iso-LSD) in a standard mixture. Although the separation of these compounds was not complete (Upper Panel), they could be flier differentiated by their parent masses and the masses of the predominant fragment (Middle & Lower panels).

Figure 7:
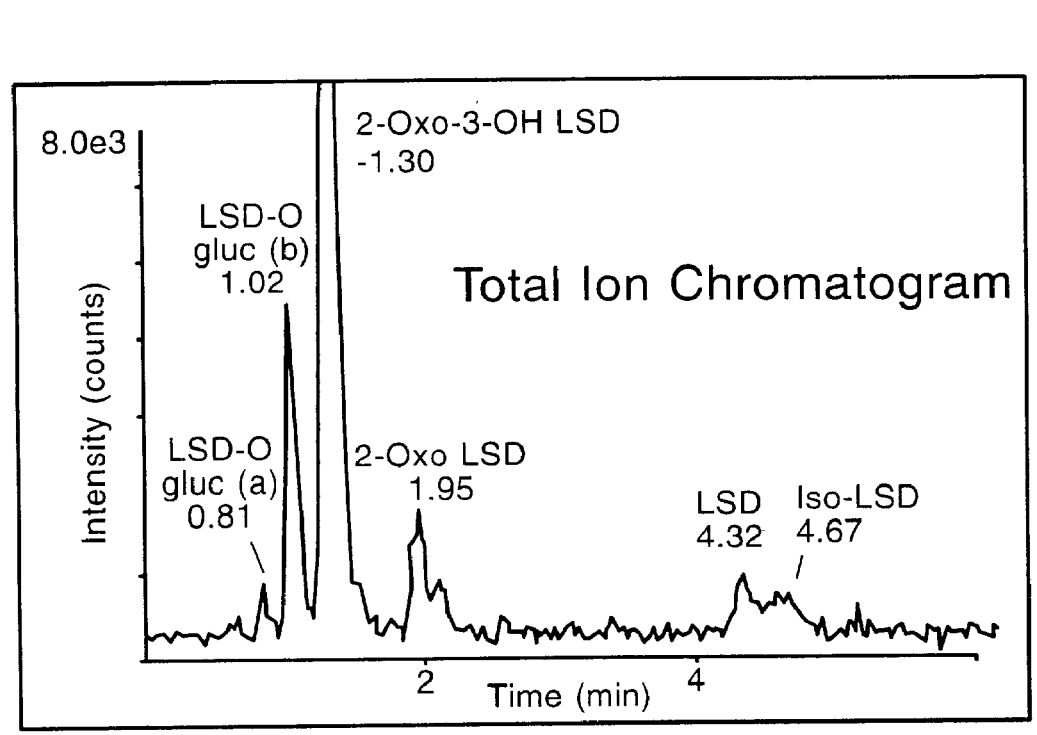
FIG. 7 (Upper Panel) is a graph showing reverse-phase HPLC/MS/MS separation of LSD and its metabolites immunoextracted from urine (Total ion chromatograph). Six major peaks are observed. The two early eluting peaks have mass values equal to LSD plus oxygen plus glucuronic acid.
Figure 7:
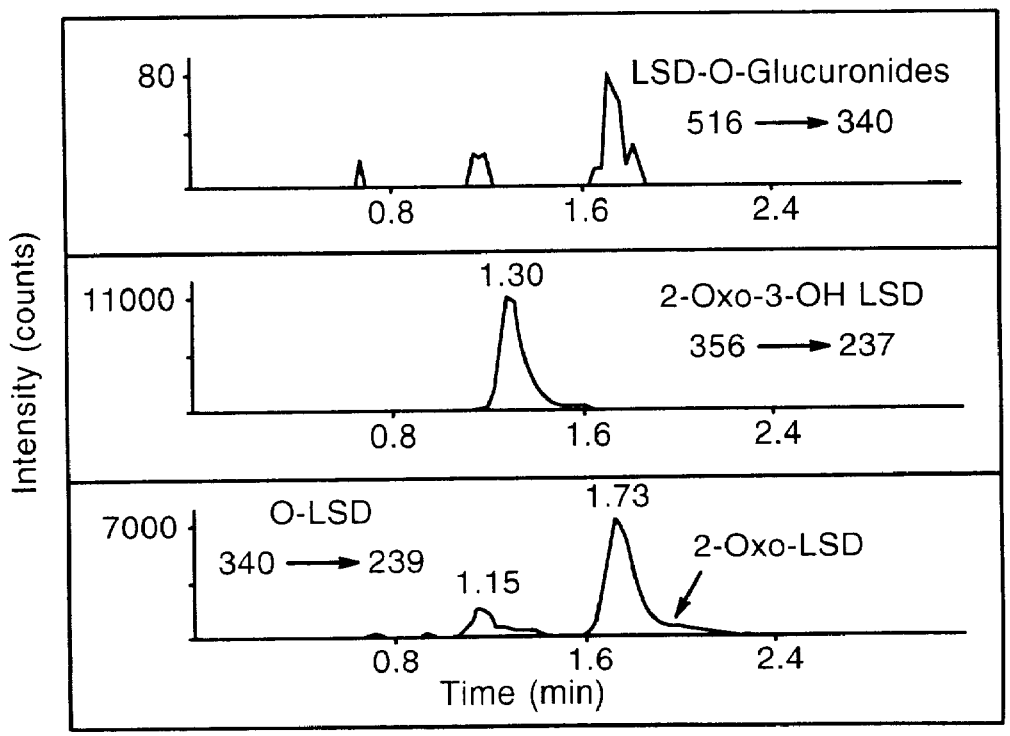

The immunoaffinity extract from pharnacokinetic study samples was analyzed by this HPLC/MS/MS method. Six peaks were observed (FIG. 7, Upper Panel):

Two partially resolved, early eluting peaks (0.81 and 1.02 min), with mass values equal to LSD plus oxygen plus glucuronic acid (i.e., hydroxy-LSD glucuronide);

A large peak corresponding to 2-oxo, 3-hydroxy LSD (a known metabolite of LSD);

A small peak corresponding to 2-oxo LSD; and

Small peaks corresponding to LSD and iso-LSD

Although unlikely, the first pair of peaks could have included a glucuronide of 2-oxo LSD. This was ruled out by treatment of the peaks with glucuronidase, followed by analysis by LC/MS/MS. The results (FIG. 7, Lower 3 panels) show that the hydroxy-LSD compounds produced by glucuronidase treatment (mass =340) elute at 1.15 and 1.73 min, which is distinct from 2-oxo LSD.

These results demonstrate that the 19A7 antibody recognizes the LSD metabolites 13-hydroxy LSD glucuronide and 14-hydroxy LSD glucuronide. This is believed to be the first antibody demonstrated to have substantial cross-reactivity with glucuronide derivatives of LSD. It is surprising that the bulky, negatively charged glucuronic acid side chains would be considered likely to interfere with binding of the metabolite to the antibody.

As illustrated in the following examples, it is advantageous to be able to detect glucuronide derivatives of LSD, since this extends the time window in which a previous administration of LSD can be detected. The glucuronide derivatives can be obtained by immunoaffinity purification of human urine samples, as illustrated above, or from the urine or bile of experimental animals administered LSD. Antibodies with substantial cross-reactivity to glucuronide can be detected not only by inmunoextraction, but by using the glucuronide derivative in the screening assay of antibody clones raised either against LSD, or against the glucuronide derivatives themselves conjugated to an immunogenic carrier, preferably through the N-1 position, the 2-position (via the Mannich reaction), or the 6-position. Glucuronide reagent conjugates can be used with the selected antibodies in a direct assay for the metabolite. Alternatively, an antibody that cross-reacts with both the LSD and the glucuronide derivatives (such as the 19A7 antibody) can be used in an immunoassay with LSD conjugated to a protein, enzyme polypeptide (such as an intact enzyme or enzyme donor), a solid surface, a radioisotope, or a fluorescent label. Because of the cross-reactivity of the antibody, both LSD and the metabolites will be detected.

EXAMPLE 14

A competitive immunoassay detecting a distinct urinary metabolite

In this example, experiments were performed to better define the time course of excretion of LSD metabolites in urine, and the ability of various immunoassays to detect them.

Individuals were administered LSD, and urine samples were collected over a 4-day period. The samples were assayed using the LSD enzyme-complementation immunoassay described in Examples 9 and 10 using monoclonal antibody 19A7. The samples were also measured using the DPC radioimmunoassay ("Coat-A-Count"® LSD assay, by Diagnostic Products Company) according to manufacturer's directions, and by GC/MS.

Results are shown in the following table in terms of LSD equivalents (translating the signal generated using a standard curve obtained with known concentrations of LSD).

TABLE 4

|       | Time hrs | CEDIA LSD ng/ml | DPC RIA LSD ng/ml | GC/MS LSD ng/ml |
|-------|----------|-----------------|-------------------|-----------------|
| SW U1 | 0        | 0.00            | 0.00              | 0.00            |
| SW U2 | 2        | 3.40            | 0.93              | 0.33            |
| SW U3 | 4        | 3.60            | 1.12              | 0.54            |
| SW U4 | 6        | 12.20           | 3.79*             | 0.52            |
| SW U5 | 8        | 3.30            | 0.98              | 0.71            |
| SW U6 | 10       | 10.70           | 4.12*             | 0.76            |
| SW U7 | 12       | 12.50           | 8.34*             | 1.77            |
| SW U8 | 24       | 12.70           | 13.49*            | 1.42            |
| SW U9 | 36       | 1.01            | 0.38              | 0.11            |
| SW U10| 48       | 0.67            | 0.15              | 0.04            |
| SW U11| 60       | 0.14            | 0.00              | 0.02            |
| SW U12| 72       | 0.13            | 0.00              | 0.00            |
| SW U13| 84       | 0.09            | 0.00              | ***             |
| SW U14| 96       | 0.09            | 0.04              | 0.01            |
| JS U1 | 0        | 0.00            | 0.06              | 0.00            |
| JS U2 | 2        | 1.70            | 0.60              | ***             |
| JS U3 | 4        | 8.30            | 3.01              | 0.39            |
| JS U4 | 6        | 7.70            | 2.17              | 0.37            |
| JS U5 | 8        | 5.20            | 1.40              | 0.38            |
| JS U6 | 10       | 10.60           | 5.99*             | 0.64            |
| JS U7 | 12       | 6.00            | 3.09*             | 0.52            |
| JS U8 | 24       | 6.40            | 3.49*             | 0.34            |
| JS U9 | 36       | 0.34            | 0.06              | 0.03            |
| JS U10| 48       | 0.26            | 0.25              | 0.01            |
| JS U11| 60       | 0.15            | 0.08              | 0.00            |
| JS U12| 72       | 0.73            | 0.50              | 0.02            |
| JS U13| 84       | 0.03            | 0.00              | 0.00            |
| JS U14| 96       | 0.07            | NA                | 0.00            |

*The RIA high calibrator is 3.0 ng/ml, values above 3.0 ng/ml are only estimates
***No value available for this sample The first sample shows a significant improvement in LSD sensitivity with 48 h time point still above the 0.5 ng/mL cut-off, as it reads 0.67 ng/mL in the CEDIA® assay. The DPC assay reads 0.38 ng/mL are 36 h, which is below the cut-off for this assay which is 0.5 ng/mL. The DPC assay detects LSD or LSD metabolites only up to the 24 h time point. The GC/MS results indicate that LSD has essentially disappeared after 24 h. The sensitivity of the CEDIA® assay after about the 24 h time point is attributable principally to an LSD metabolite.

This invention includes amongst its embodiments a set of reagents for use in an immunoassay for quantifying LSD or excreted metabolites of LSD, such as may be present in a urine sample of an individual suspected of having been administered LSD. The reagents include an antibody, preferably a monoclonal antibody, capable of binding the conjugate of the first reagent in a manner that is measurably inhibitable by LSD and one or more LSD metabolites.

Preferred characteristics of the antibody, the reagent combination, and the assay performed using the reagents are that the median relative level of LSD and LSD metabolites measurable in urine samples taken from a subject 36 hours after administration of LSD by the competitive immunoassay is at least 3%, preferably 5%, and more preferably 10% of the highest levels of LSD and LSD metabolites measurable in urine samples from the same subject within the first 24 h after the administration. Other preferred characteristics are that the median relative level of LSD and LSD metabolites measurable in urine samples taken from a subject 48 hours after administration of LSD by the competitive immunoassay is at least 1%, preferably 3%, and more preferably 5% of the highest levels of LSD and LSD metabolites measurable in urine samples from the same subject within the first 24 h after the administration. Other preferred characteristics are that the ratio of LSD measured at 48 hours to the level measured at 24 hours is at least about 2 times, preferably at least about 4 times, more preferably at least about 10 times what is measured by GC/MS.

Other preferred characteristics of the antibody are that it be specific for a glucuronic acid conjugate of LSD, particularly hydroxy-LSD glucuronide, wherein the glucuronic acid conjugate is at least 5% cross-reactive, preferably at least about 10% cross-reactive, more preferably at least about 20% cross reactive, even more preferably at least about 50% cross reactive, still more preferably 100% cross reactive or more, when used to determine the concentration of LSD or LSD metabolite in a competitive immunoassay. Cross reactivity is determined in a quantitative immunoassay by establishing a standard curve using known dilutions of the target analyte, then using the standard curve to calculate the apparent concentration of the interfering substance present in various known amounts in samples assayed under similar condition. It will be appreciated that antibodies with the ability to bind LSD metabolites can also be used in assays to measure LSD metabolites directly; for example, in a competitive radioimmunoassay wherein the metabolite in the sample competes with radioisotopically labeled LSD glucuronide.

The ability of the materials and methods of this invention to detect LSD metabolites is demonstrated in experiments using a sample containing the metabolite but known by GC/MS to be essentially free of the LSD parent compound. In the following experiment, the results of the CEDIA® are compared with those of the DPC assay, and with those obtained using the "Abuscreen"® radioimmunoassay by Roche. While the amount of metabolite in the sample is not known in absolute terms, the behavior is tested by dilution analysis. Results are given in terms of LSD equivalents.

TABLE 5

| Analyte | LSD ng/ml CEDIA | LSD ng/ml DPC RIA | LSD ng/ml Abuscreen RIA |
|---|---|---|---|
| LSD Metabolite | 1.32 | 0.14 | 0.62 |
| diluted 1:3* | 0.50 | 0.03 | 0.23 |

The data indicate that the reagents and methods of the invention recognize the metabolite in the sample about 10-fold better than does the DPC assay, and about 2.5 fold better than the Abuscreen® assay.

The ability to detect a urinary metabolite with a longer half-life is of considerable benefit in evaluating an individual's exposure to LSD. Immunoassay kits of the invention can be used for determining whether a subject has been administered LSD by conducting an immunoassay on a urine sample and then correlating any LSD or LSD metabolite detected with administration of LSD to the subject. A metabolite with a longer biological half-time will provide evidence of a previous exposure even if the sample has been obtained several days after the exposure. Where the sample contains the metabolite, the time between exposure and sample collection can be at least 2 days, and as much as 3 or 4 days later, depending on the amount of LSD administered, urine storage time, and the metabolic rate of the individual tested. To the extent that the metabolite also appears in blood before excretion by the kidney, the materials of this invention can also be used to measure its presence in plasma or serum samples or other biological fluids, and then correlate its presence with LSD exposure. Ultimate interpretation of the results is the responsibility of the managing clinician.

All publications and patent applications mentioned in this specification are hereby incorporated by reference to the same extent as if each individual publication or patent application were specifically and individually indicated to be incorporated by reference. The invention now being fully described, it will be understood that the specification and examples are illustrative but not limiting of the present invention, and that modifications and changes will suggest themselves to those skilled in the art but will not depart from the spirit and scope of the appended claims.

What is claimed as the invention is:

1. An immunoassay method for determining the presence of LSD or LSD metabolites in a sample comprising a) contacting the sample with an antibody to LSD or LSD metabolites, wherein said antibody is raised to an LSD-protein conjugate having a protein carrier conjugated to said LSD at the N-1 position of said LSD, said LSD-protein conjugate having the structure

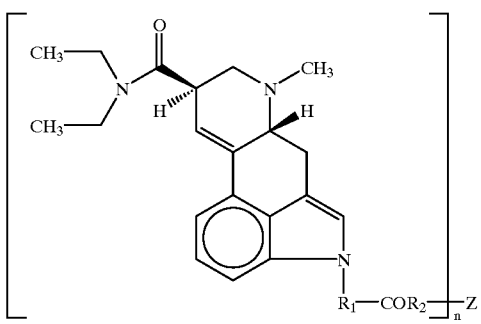

wherein R1 is an alkyl cycloalkyl, or aryl group having 1 to 10 carbon atoms;
wherein R2 is a bond or

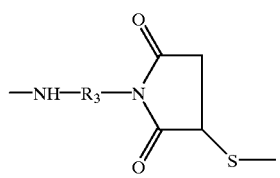

wherein R3 is an alkyl, cycloalkyl, or aryl group having 2 to 10 carbon atoms;
wherein Z is selected from the group consisting of an immunogenic carrier substance, an enzyme donor polypeptide, and a label; and
n is 1 to p wherein p is the molecular weight of Z/1000;
b) contacting the antibody with said LSD-protein conjugate;
c) measuring complexes formed between the conjugate and the antibody by contacting the complexes with a detection reagent, and thereby detecting a first signal generated by the complexes; and
d) determining an amount of LSD or LSD metabolites in the sample by comparing the first signal detected to a second signal detected using a known concentration of LSD or LSD metabolites;
wherein one or more of the following are characteristics of the antibody:
   (i) the antibody is less than 1% crossreactive with chlorpromazine;
   (ii) the antibody is less than 0.1% crossreactive with ergotamine;
   (iii) the antibody binds the conjugate such that the frequency of false positive reactions with clinical urine samples not containing LSD is less than 4%;
   (iv) the antibody binds the conjugate such that the median relative level of LSD and LSD metabolites measurable in urine samples taken from a subject 36 hours after administration of LSD is at least 5% of the highest levels of LSD and LSD metabolites measurable in urine samples from the same subject within the first 24 h after the administration; or
   (v) the antibody is capable of binding the conjugate in a manner that is inhibitable by a glucuronide derivative of LSD.

2. The immunoassay method of claim 1, wherein the antibody is a monoclonal antibody.

3. The immunoassay method of claim 1, wherein the LSD protein conjugate comprises LSD conjugated to an enzyme or an enzyme donor polypeptide.

4. The immunoassay method of claim 1, wherein the LSD-protein conjugate comprises a protein and LSD, and the protein is conjugated to the N-1 position of the LSD.

5. The immunoassay method of claim 1, wherein the antibody is less than 1% crossreactive with chlorpromazine.

6. The immunoassay method of claim 1, wherein the antibody is less than 0.1% crossreactive with ergotamine.

7. The immunoassay method of claim 1, wherein the antibody binds the conjugate such that the frequency of false positive reactions with clinical urine samples not containing LSD is less than 4%.

8. The immunoassay method of claim 1, wherein the sample is a sample urine.

9. The immunoassay method of claim 1, which is a homogeneous assay method.

10. The immunoassay method of claim 1, which is a separation assay method.

11. The immunoassay method of claim 1, which is an enzyme assay method.

12. The immunoassay method of claim 1, wherein the LSD-protein conjugate is an LSD-enzyme donor conjugate, and the measuring in step c) comprises contacting ezmye remaining conjugate with an enzyme acceptor to form an enzyme complex; contacting any enzyme complex with a substrate therefor; and measuring the rate of conversion of the substrate to a product.

13. An immunoassay method for determining the presence of LSD or LSD metabolites in a sample comprising
   a) contacting the sample with an antibody to LSD or LSD metabolites, wherein said antibody is raised to an LSD-protein conjugate having a protein carrier conjugated to said LSD at the N-1 position of said LSD, said LSD-protein conjugate having the structure

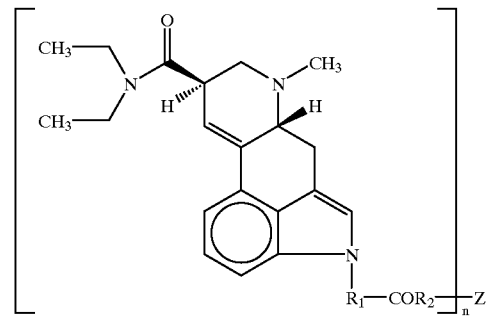

wherein R1 is an alkyl cycloalkyl, or aryl group having 1 to 10 carbon atoms:
wherein R2 is a bond or

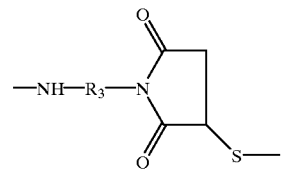

wherein R3 is an alkyl, cycloalkyl, or aryl group having 2 to 10 carbon atoms;
wherein Z is selected from the group consisting of an immunogenic carrier substance, and enzyme donor polypeptide, and a label; and
n is 1 to p wherein p is the molecular weight of Z/1000;
   b) contacting the antibody with said LSD-protein conjugate;

c) measuring complexes formed between the conjugate and the antibody by contacting the complexes with a detection reagent, and thereby detecting a first signal generated by the complexes; and d) determining an amount of LSD or LSD metabolites in the sample by comparing the first signal detected to a second signal detected using a known concentration of LSD or LSD metabolites;

wherein one or more of the following are characteristics of the antibody:

(i) the antibody binds the conjugate such that the median relative level of LSD and LSD metabolites measurable in urine samples taken from a subject 36 hours after administration of LSD is at least 5% of the highest levels of LSD and LSD metabolites measurable in urine samples from the same subject within the first 24 h after the administration; or (ii) the antibody is capable of binding the conjugate in a manner that is inhibitable by a glucuronide derivative of LSD.

14. The immunoassay method of claim 13, wherein the LSD conjugate comprises LSD conjugated to an enzyme or an enzyme donor polypeptide.

15. The immunoassay method of claim 1, wherein the LSD conjugate comprises LSD conjugated to a radioisotope or a fluorescent label.

* * * * *